United States Patent
Afran

[19]

[11] Patent Number: 6,158,863
[45] Date of Patent: Dec. 12, 2000

[54] PEDIATRIC RETINOSCOPE

[75] Inventor: Scott I. Afran, 688 White Plains Rd., Suite 219, Scarsdale, N.Y. 10583

[73] Assignee: Scott I. Afran, Scarsdale, N.Y.

[21] Appl. No.: 09/422,419

[22] Filed: Oct. 21, 1999

[51] Int. Cl.[7] ........................................... A61B 3/08
[52] U.S. Cl. ........................................................ 351/202
[58] Field of Search ................................ 351/202, 201, 351/208, 209, 210, 214, 221, 246, 243, 239

[56] References Cited

U.S. PATENT DOCUMENTS

| | | |
|---|---|---|
| 1,625,075 | 4/1927 | Clement et al. . |
| 1,990,218 | 2/1935 | Bailey . |
| 3,724,931 | 4/1973 | Nevyas et al. . |
| 4,093,359 | 6/1978 | Ketcham . |
| 4,274,716 | 6/1981 | Gammon ................................. 351/243 |
| 4,536,065 | 8/1985 | Sheingorn . |
| 4,747,682 | 5/1988 | Reese . |
| 4,758,080 | 7/1988 | Howland . |
| 4,979,812 | 12/1990 | Reese . |
| 5,173,724 | 12/1992 | Bonham et al. . |
| 5,552,842 | 9/1996 | Ginsburg et al. . |
| 5,764,340 | 6/1998 | Hofeldt . |

*Primary Examiner*—George Manuel
*Attorney, Agent, or Firm*—Kalow & Springut LLP

[57] ABSTRACT

Retinoscope with visual and auditory components is disclosed for use in providing a fixation point for the patient when undergoing a retinoscopy procedure.

16 Claims, 2 Drawing Sheets

PEDIATRIC RETINOSCOPE

BACKGROUND OF THE INVENTION

Amblyopia, more commonly known as 'lazy eye', refers to a condition where young children develop decreased vision in one or both eyes. In amblyopia, the structural integrity of the eye is usually normal. However, in many cases children develop amblyopia because of a large difference in the focusing power between the two eyes. This type of amblyopia is often referred to by ophthalmologists as anisometropic amblyopia because it is caused by the difference in the refraction between each eye.

Amblyopia affects up to 4 percent of all children in the United States. However, it is amenable to treatment with early diagnosis. To properly treat a child for amblyopia, it is very important to make the diagnosis and initiate treatment when the child is very young. Often times, however, the diagnosis of amblyopia will not be made until the vision in one eye deteriorates to the point that one eye pivots inwardly or outwardly. This visual defect is termed strabismus, and is commonly referred to in the lay literature by the term 'lazy eye'. Unfortunately, when turning of an eye occurs, it is often difficult to correct the problem, and only partial success is normally achieved.

With normal vision, both eyes will 'aim' at the same points of interest, and the brain will then combine the 'picture' taken by each eye into a single three-dimensional image. This three-dimensional image is what allows one to have depth perception. However, when one eye turns, two different 'pictures' are sent to the brain, and in a child, the brain learns to ignore the image of the misaligned eye and sees only the image from the straight or better seeing eye, and this results in a loss of depth perception, and ultimately loss of vision in the deviating eye. This loss of vision is often permanent, and may render the patient legally blind in the affected eye.

In view of the frequency of this problem, and the need for this condition to be detected early in order for the patient to have the greatest chance of total vision correction [see *J Ophthalmic Nurs Technol* 17(6):227 (1998), *Can Fam Physician* 44:337 (1998), and *Pediatr Clin North Am* 45(4):993 (1998)] pediatricians and school nurses often screen children for amblyopia at between 3 and 4 years of age. Screening programs utilizing conventional materials and protocols such as Snellen charts and retinoscopy are highly successful in identifying children who are at risk for amblyopia. However, treatment is complicated by the fact that the children are often uncooperative or do not understand the examination techniques. In order to prescribe glasses for a young child it is necessary to evaluate the light reflex which comes off the retina. This is normally accomplished by a retinoscopic examination that allows for light reflexes coming off of the retina to be examined and thereby determine the refractive state of the eye. The ophthalmologist or other licensed professional can then prescribe glasses for the patient as needed. However, this technique is difficult to perform in children less than 4 years of age because they are often frightened of the device and do not want the ophthalmologist, pediatrician, nurse or other licensed professional to hold lenses or examination instruments close to their eyes. The use of a retinoscope is absolutely necessary in order to rule out amblyopia in very young children less than 4 years of age.

Prior attempts to attract, maintain and fix the gaze of a patient during an ophthalmic examination have included such devices as a small animatable fixation target, such as a small toy animal with movable body parts, that is held in the mouth of the licensed professional in front of the patient undergoing the ophthalmic examination. Such a device, as described in U.S. Pat. No. 4,093,359, for example, is obviously unsatisfactory and cumbersome for the licensed professional.

Other attempts to provide fixation devices for patients also exhibit limitations. For example, a rotatable disk upon which is drawn a downward spiral and will draw the observer's attention to the center of the spiral when rotated, or mechanical figures that are capable of movement when activated may also be used as fixation devices for patients, especially young children, undergoing ophthalmologic examinations. However, such devices normally require that they be mounted behind the licensed professional; are fairly large; and are difficult for the licensed professional to operate and control during the examination.

SUMMARY OF THE INVENTION

It is therefore a primary aspect of the present invention to describe an instrument for the examination of an eye that is capable of being hand-held by the licensed professional during the examination.

It is an additional aspect of the present invention that the instrument contain a fixation point located on the instrument that will attract, maintain and fix the gaze of a patient during an ophthalmic examination.

It is still an additional aspect of the present invention that the instrument be one by which a retinoscopic examination of the eye may be made by the licensed professional.

BRIEF DESCRIPTION OF THE DRAWINGS

These and other aspects, advantages and features of the present invention will become readily apparent to, and more fully understood by, those skilled in the art by reference to the following detailed description of the invention, taken in conjunction with the accompanying figures which are provided solely for the purpose of illustration and not for the purpose of limiting the scope of the present invention in any manner, and in which.

Figures 1, 2:
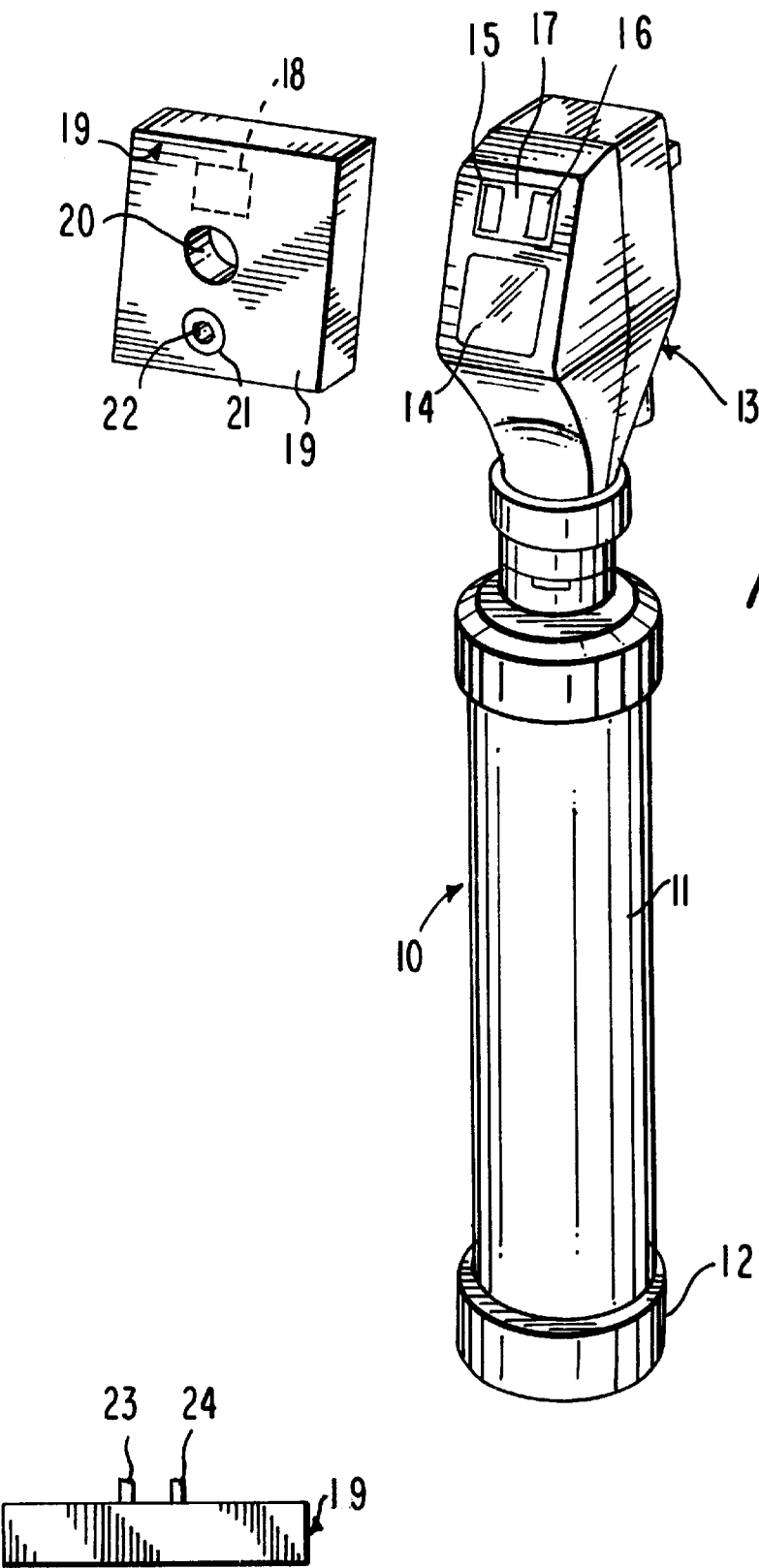
FIG. 1 depicts a three-quarter exploded perspective view of an instrument according to the present invention.
FIG. 2 depicts a top planar view of one portion of the instrument according to the present invention.

DESCRIPTION OF THE INVENTION:

As generally depicted in FIG. 1., the instrument 10 according to the present invention consists of a hollow cylindrical body 11 that functions as both a handpiece to hold the instrument and a container to hold a single-use or rechargeable battery for the operation of the instrument as is found in conventional retinoscopes. The lower portion of body 11 terminates in a female cap 12, and the upper portion of body 11 terminates in an upper optical head 13 as would be found in a conventional retinoscope.

The upper optical head 13 comprises a front face 35 which when in use will face the patient whose eye is being examined, and a rear face 36 which when in use will face the professional conducting the examination. Adjacent the front face 35 of the upper optical head is located a removable fixation device 19 according to the present invention which carries two metallic male plug prongs 23 and 24 on its rear surface which are adapted to fit into two female receptacle metallic plug members 15 and 16 located within a gripping indentation 17 within the surface of the front face. When assembled, fixation device 19 will be held to the front face 35 of optical head 13 by the friction-fit of male plug prongs 23 and 24 into the female receptacle plug members 15 and 16, and electrical current will be able to be transferred from the battery within body 11 to the electronics contained in device 19.

Fixation device 19 also comprises an opening 20 passing from the front to the back surfaces thereof which, when the instrument according to the present invention is assembled, will align in juxtaposition with front window 14 manufactured of a clear transparent material that may or may not have a magnifying power; a front surface opening 21 which holds a light emitting diode 22, i.e., the 'fixation point' of said device; and speaker screen 18, which may merely be a number of small openings in the front surface of device 19 to allow for sound to pass from an internally held speaker 37 and through device 19. Internally, fixation device 19 contains connective wires 28 to allow electrical current to travel from each male prong (23 and 24) to a computer chip 29. Wires 30 containing chip 29 to the LED 22, and wires 31 connect chip 29 with speaker 37. Chip 29 is manufactured to contain programmed electronic circuits to activate LED 22 to produce light, and speaker 37 to produce sound.

Figure 3:
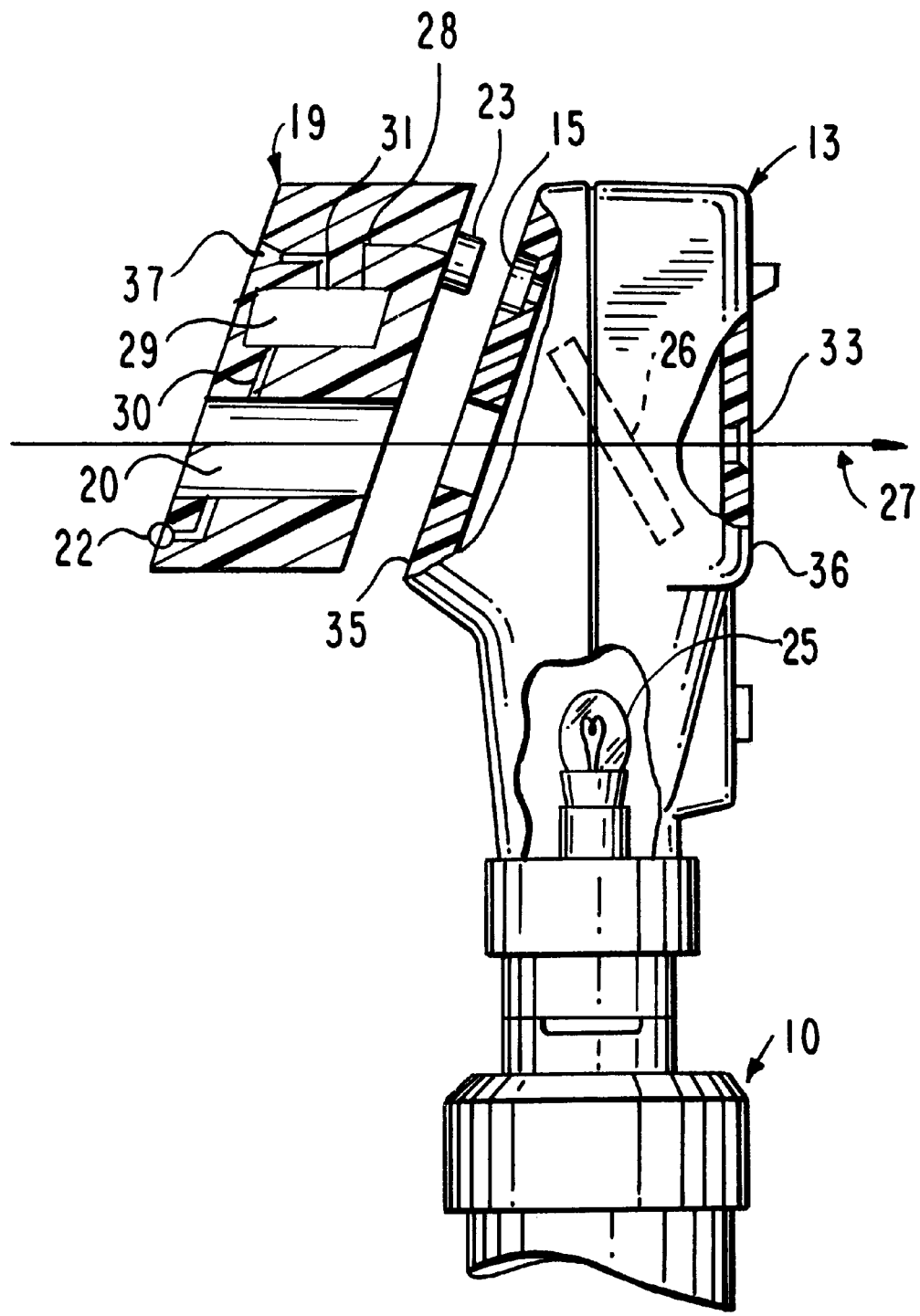
FIG. 3 depicts a cross-sectional exploded side elevation view taken along the plane of the optical path of the upper portions of an instrument according to the present invention

Alternatively, while upper optical head 13 and fixation device 19 are depicted in FIG. 1 and FIG. 3 as being separate components, if upper optical head 13 is designed to be manufactured with sufficient depth, it is well within the capabilities of those skilled in the art to combine the electronics and components of fixation device 19 directly within optical head 13, i.e., optical head 13 may be manufactured to contain LED 22, speaker 37, and computer chip 29 within optical head 13 as a single unit, which single unit will generally conform in appearance to that of separate optical head 13 and fixation device 19 when joined, i.e., assembled, together.

Optical head 13, as conventionally found in present retinoscopes, includes a light source 25 which is preferably a halogen light of high intensity. Light source 25 is arranged within optical head 13 to direct a beam of light at a beam splitter 26 with the result that a light beam will be redirected through front wall window 14 along light path 27. When assembled, or when manufactured as a single instrument, and in use, light path 27 will pass through opening 20 toward the eye of the patient undergoing examination. In either manufacture, i.e., as a separate fixation device 19 or incorporated within optical head 13 as a single instrument, the electronics contained in the instrument according to the present invention will be powered, as in conventional retinoscopes, when the user turns on light source 25. The user will conduct his or her examination of the patient's eye by looking through an open rear wall window 33 that is centered about light path 27. As window 14, window 33 is normally a transparent lens which may or may not have a magnifying power in order to enlarge the image being observed by the user during examination. Thus the licensed user can examine the patient's eye directly along the light path 27 passing through beam splitter 26. In addition, as is done conventionally during retinoscopic examination, various lenses and filters may be placed in front of light path 27 between the patient's eye and the instrument according to the present invention.

Thus, while I have illustrated and described the preferred embodiment of my invention, it is to be understood that this invention is capable of variation and modification, and I therefore do not wish or intend to be limited to the precise terms set forth, but desire and intend to avail myself of such changes and modifications which may be made for adapting the present invention to various usage's and conditions. Accordingly, such changes and modifications are properly intended to be within the full range of equivalents, and therefore within the purview of the following claims.

For example, as the instrument according to the present invention is meant to attract, maintain and fix the gaze of a patient during an ophthalmic examination, computer chip 29 may contain various programs for controlling both light 22 and/or the sound emitting from speaker 37. For example, the light program on chip 29 may be one which will cause light 22 to flash intermittently, remain at a constant intensity, or increase and decrease in intensity. In addition, the sound program on chip 29 may be one which results in various tones, sounds and volumes as, for example, in the examination of young children it may be preferred that the program reproduce animal sounds that are familiar to young children, and in working with older children the preferred program may be one that reproduces sounds associated with science fiction movies. Such programming and manufacture of computer chips to control LED's and sounds is well known by those skilled in the art. Also as depicted in FIG. 1, the fixation LED source 22 is located below the front opening 20, and the speaker location generally indicated at 18 is above the front opening 20. However, the specific locations of the opening and speaker are merely illustrative, and in actuality they may be reversed, i.e., LED 22 may be located above or to either side of front opening 20, and in similar fashion, the speaker location generally indicated at 18 may be located below or to either side of front opening 20. In one alternative placement, for example, the speaker 37 may be located behind LED 22 and in opening 21. In addition to being a LED, the fixation point may also be flat liquid crystal display panel as is found, for example, in hand-held computer games, having an animated figure or other character(s) to attract, maintain and fix the gaze of a patient during the ophthalmic examination.

The terms and expressions which have been employed in the foregoing specification are used as terms of description and not of limitation, and thus there is no intention, in the use of such terms and expressions, of excluding equivalents of the features shown and described, or portions thereof; the scope of the invention being defined and limited only by the claims which follow.

Having thus described my invention and the manner and process of making and using it in such full, clear, concise, and exact terms so as to enable any person skilled in the art to which it pertains, or with which it is most nearly connected, to make and use the same, I claim:

1. A diagnostic medical instrument for use in examining the eye of a patient which comprises a handle portion;

an optical head attached to said handle portion and having a front and rear face;

an opening passing through said front and rear faces and being centered on a single optical path;

an electrical current source;

a light source;

a light beam splitter located across said optical path so that light emitted from said light source will pass through the opening in said front face along said optical axis; and a gripping attachment on said front face of said optical head and comprising a female receptacle plug member having two prong receptacles adapted to receive and hold a fixation component having two prongs adapted to be inserted and held in said prong receptacles.

2. A diagnostic medical instrument according to claim 1 wherein said two prong receptacles are adapted to transmit an electric current to said fixation component.

3. A diagnostic medical instrument according to claim 2 wherein the handle portion contains battery means for providing electrical current to the light source each of the two prong receptacles.

4. A fixation component for attachment to the front face of a diagnostic medical instrument used in examining the eye of a patient and having an optical path passing through the front and rear faces of said instrument; said component comprising means for attaching the rear surface of said component to the front face of said instrument including means for transferring an electrical current from said instrument to said component;

an opening passing through said component and having an optical path which will coincide with the optical path passing through the front and rear faces of said instrument when said component and instrument are assembled for use; and a fixation point to attract, maintain and fix the gaze of a patient during an ophthalmic examination on the front surface of component.

5. A fixation component according to claim 4 which also comprises an audio source for generating a sound to aid in attracting, maintaining and fixing the gaze of a patient during an ophthalmic examination.

6. A fixation component according to claim 5 wherein said fixation point is a light emitting diode, and the audio source is a audio speaker located within the body of said component.

7. An improved diagnostic instrument for examining the eye of a patient which comprises a handle connected to an instrument optical head, a light source, and means for directing a beam of light along an optical axis to the patient's eye, the improvement comprising:

a fixation component having at least one electrically-activated fixation point to attract, maintain and fix the gaze of a patient during an ophthalmic examination on the front surface of component; and an opening passing through said component to allow a beam of light from said light source to be directed along said optical axis to the patient's eye.

8. An improved diagnostic instrument according to claim 7 wherein at least one electrically-activated fixation point is a light source.

9. An improved diagnostic instrument according to claim 7 wherein at least one electrically-activated fixation point is an audio source.

10. An improved diagnostic instrument according to claim 7 wherein one electrically-activated fixation point is a light source and another electrically-activated fixation point is an audio source.

11. An improved diagnostic instrument according to claim 7 wherein said component is integrally manufactured with said optical head.

12. An improved diagnostic instrument according to claim 7 wherein said component is separately manufactured from said optical head and may be disengaged from said optical head by the user of said instrument.

13. A diagnostic medical instrument for use in examining the eye of a patient which includes a handle portion;

an optical head attached to said handle portion and having a front and rear face;

an opening passing through said front and rear faces and being centered on a single optical path;

an electrical current source;

a light source;

a light beam splitter located across said optical path so that light emitted from said light source will pass through the opening in said front face along said optical axis;

a computer chip connected to said current source and having a program to provide an electrical output to a light means located at the front face of said optical head.

14. A diagnostic medical instrument according to claim 13 wherein said light means is an LED.

15. A diagnostic medical instrument according to claim 13 wherein said computer chip further provides an electrical output to an audio means located at the front face of said optical head.

16. A diagnostic medical instrument according to claim 13 wherein said audio means is a speaker located with the body of said optical head.

* * * * *